US006532381B2

(12) United States Patent
Bayer et al.

(10) Patent No.: US 6,532,381 B2
(45) Date of Patent: Mar. 11, 2003

(54) PATIENT MONITOR FOR DETERMINING A PROBABILITY THAT A PATIENT HAS ACUTE CARDIAC ISCHEMIA

(75) Inventors: Brian J. Bayer, Menomonee Falls, WI (US); Areef Ahmed Bin Moin, Waukesha, WI (US); Patrick Van Ryzin, Pewaukee, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 5 days.

(21) Appl. No.: 09/681,112

(22) Filed: Jan. 11, 2001

(65) Prior Publication Data

US 2002/0133087 A1 Sep. 19, 2002

(51) Int. Cl.[7] ................................................. A61B 5/04
(52) U.S. Cl. ....................................................... 600/515
(58) Field of Search ................................. 600/509, 513, 600/515–518

(56) References Cited

U.S. PATENT DOCUMENTS

| | | | |
|---|---|---|---|
| 4,679,144 A | | 7/1987 | Cox et al. ................. 600/516 |
| 4,680,708 A | | 7/1987 | Ambos et al. ............. 600/509 |
| 4,930,075 A | * | 5/1990 | Kortas .................. 364/413.06 |
| 4,957,115 A | | 9/1990 | Selker .................... 600/509 |
| 5,365,426 A | * | 11/1994 | Siegel et al. ............. 600/509 |
| 5,377,687 A | * | 1/1995 | Evans et al. ............. 600/513 |
| 5,437,285 A | * | 8/1995 | Verrier et al. ............ 128/702 |
| 5,501,229 A | * | 3/1996 | Selker et al. ............ 600/508 |
| 5,683,424 A | * | 11/1997 | Brown et al. ............... 607/5 |
| 6,339,720 B1 | * | 1/2002 | Anzellini et al. .......... 600/517 |

OTHER PUBLICATIONS

"Dash 2000/3000 Portable Monitoring", GE Marquette Medical Systems Company, Mar. 1999.
"Model M1791A, Acute Cardiac Ischemia Time–Insensitive Predicitve Instrument (HP ACI–TIPI)", Hewlett Packard Company, 1996.
Selker, H.P. et al., "Use of the Acute Cardiac Ischemia Time–Insensitive Predictive Instrument (ACI–TIPI) to Assist with Triage of Patients with Chest Pain or Other Syptoms Suggestive of Acute Cardiac Ischemia", Annals of Internal Medicine, Dec. 1, 1998.
"HP Introduces First ECG Instrument for Predicting Heart Attack Probability", Hewlett–Packard Company, Mar. 25, 1996.
Selker, H.P. et al., "A Tool for Judging Coronary Care Unit Admission Appropriateness, Valid for Both Real–Time and Retrospective Use", Medical Care, vol. 29, No. 7, pp. 610–627, 1991.

\* cited by examiner

Primary Examiner—Carl Layno
(74) Attorney, Agent, or Firm—Michael Best & Friedrich LLP

(57) ABSTRACT

A patient monitor for determining a probability that a patient has acute cardiac ischemia including an input device connectable to a patient to acquire electrocardiogram (ECG) signals from the patient, an instrumentation amplifier connected to the input terminal to combine the signals and to generate at least one ECG lead, and an analysis module. The analysis module is operable to continuously read the ECG lead, to analyze a portion of the ECG lead for a period of time, and to calculate a probability that the patient has acute cardiac ischemia based at least in part on the analyzed portion of the ECG lead.

55 Claims, 2 Drawing Sheets

PATIENT MONITOR FOR DETERMINING A PROBABILITY THAT A PATIENT HAS ACUTE CARDIAC ISCHEMIA

BACKGROUND OF INVENTION

The invention relates to a patient monitor and, particularly, a patient monitor for continuously monitoring one or more physiological signals of a patient and for determining a probability that a patient has acute cardiac ischemia based at least in part on one of the continuously monitored physiological signals.

Every day, patients arrive at an emergency room of a hospital complaining of chest pain. The chest pain may be a symptom indicating the patient is experiencing a myocardial infarction or, alternatively, the chest pain may be a symptom indicating the patient is experiencing a lesser medical condition (e.g., heartburn or indigestion). Statistics show that quickly identifying whether a patient is having a myocardial infarction may minimize the amount of damage to the heart. However, performing the necessary tests to correctly determine whether a patient is experiencing the myocardial infarction or heartburn are expensive.

One instrument used to predict whether a patient is likely experiencing a myocardial infarction is an electrocardiograph capable of calculating a probability that the patient has acute cardiac ischemia. If the patient has a high probability of acute cardiac ischemia, then the patient should be further tested to determine whether the patient is experiencing a heart attack. One instrument for determining a probability of a patient having acute cardiac ischemia is an Acute Cardiac Ischemia—Time-Insensitive Predictive Instrument (ACI-TIPI). ACI-TIPI is described in detail in Selker et al., H. P. *A Tool for Judging Coronary Care Unit Admission Appropriateness, Valid for both Real-Time and Retrospective Use: Medical Care,* Vol. 29, No. 7 July 1991), pp. 610–627 and Selker et al., H. P. *Erratum: Medical Care,* Vol. 30, No. 2 (February 1992), p. 188, both of which are incorporated herein by reference.

The ACI-TIPI calculates a score representing the probability of a patient having acute cardiac ischemia. Based on the probability of the patient having acute cardiac ischemia, an experienced doctor or technician can determine whether the patient should be admitted to the coronary care unit. Once admitted to the coronary care unit, the patient can undergo more complicated, expensive and time consuming tests to determine whether the patient is experiencing a heart attack.

Prior medical equipment having the capability of calculating a probability of a patient having acute cardiac ischemia consisted exclusively of electrocardiographs having ACI-TIPI. An example electrocardiograph capable of determining a probability that a patient has acute cardiac ischemia is the MAC™5000, which is manufactured and sold by GE Medical Systems Information Technologies, Inc. Electrocardiographs are not used for continuous, constant or ongoing patient monitoring, i.e., they typically only take a small time sample (e.g., ten to twelve seconds) of a patient's electrocardiograms (ECGs). A separate piece of medical equipment (i.e., a patient monitor) is attached to a patient for continuous, constant or ongoing monitoring of patient parameters. One such patient monitor is the DASH®2000 brand patient monitor, which is manufactured and sold by GE Medical Systems Information Technologies, Inc. Such patient monitoring devices however have not heretofore included the capability of determining the probability that a patient has acute cardiac ischemia.

SUMMARY OF INVENTION

When the patient enters the emergency room complaining of chest pains, multiple pieces of medical equipment (e.g., a patient monitor and an electrocardiograph) may be attached to the patient at any time. Attaching multiple pieces of equipment to the patient requires time for attachment, space for each piece of equipment, and coordination among the emergency room staff. In addition, the patient may be periodically moved throughout the emergency room or the hospital. Consequently, requiring an electrocardiograph to be temporarily attached to the patient requires use of extra time, space, personnel, and restricts transferability, which may affect the care provided to the patient. Therefore, it would be beneficial to have a patient monitor, and particularly a patient transport monitor, capable of determining a probability that a patient has acute cardiac ischemia.

Accordingly, the invention provides a patient monitor for determining a probability that a patient has acute cardiac ischemia. The patient monitor includes an input device connectable to a patient to continuously acquire electrocardiogram (ECG) signals from the patient, an instrumentation amplifier connected to the input terminal to combine the signals and to generate at least one ECG lead, and an analysis module. The analysis module is operable to continuously read the ECG lead, to analyze a portion of the ECG lead for a period of time, and to calculate a probability that the patient has acute cardiac ischemia based at least in part on the analyzed portion of the ECG lead.

The invention further provides a method of determining a probability that a patient has acute cardiac ischemia. The method includes the acts of providing a patient monitor having an input device connectable to a patient, acquiring electrocardiogram (ECG) signals from the patient, generating at least one ECG lead in response to acquiring the ECG signals, continuously monitoring the ECG lead, analyzing a portion of the ECG lead for a period of time, and calculating the probability that the patient has acute cardiac ischemia based at least in part on the analyzed portion of the ECG lead.

The invention further provides a software program for a patient monitor. The software program is capable of determining a probability that a patient has acute cardiac ischemia. The software program includes the acts of reading at least one electrocardiogram (ECG) lead acquired from the patient, continuously monitoring the ECG lead, analyzing a portion of the ECG lead for a period of time, and calculating the probability that the patient has acute cardiac ischemia based at least in part on the analyzed portion of the ECG lead.

Other features and advantages of the invention will become apparent to those skilled in the art upon review of the following detailed description, claims, and drawings.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of including and comprising and variations thereof herein is meant to encompass the items listed thereafter and equivalents thereof as well as additional items.

Figure 1:
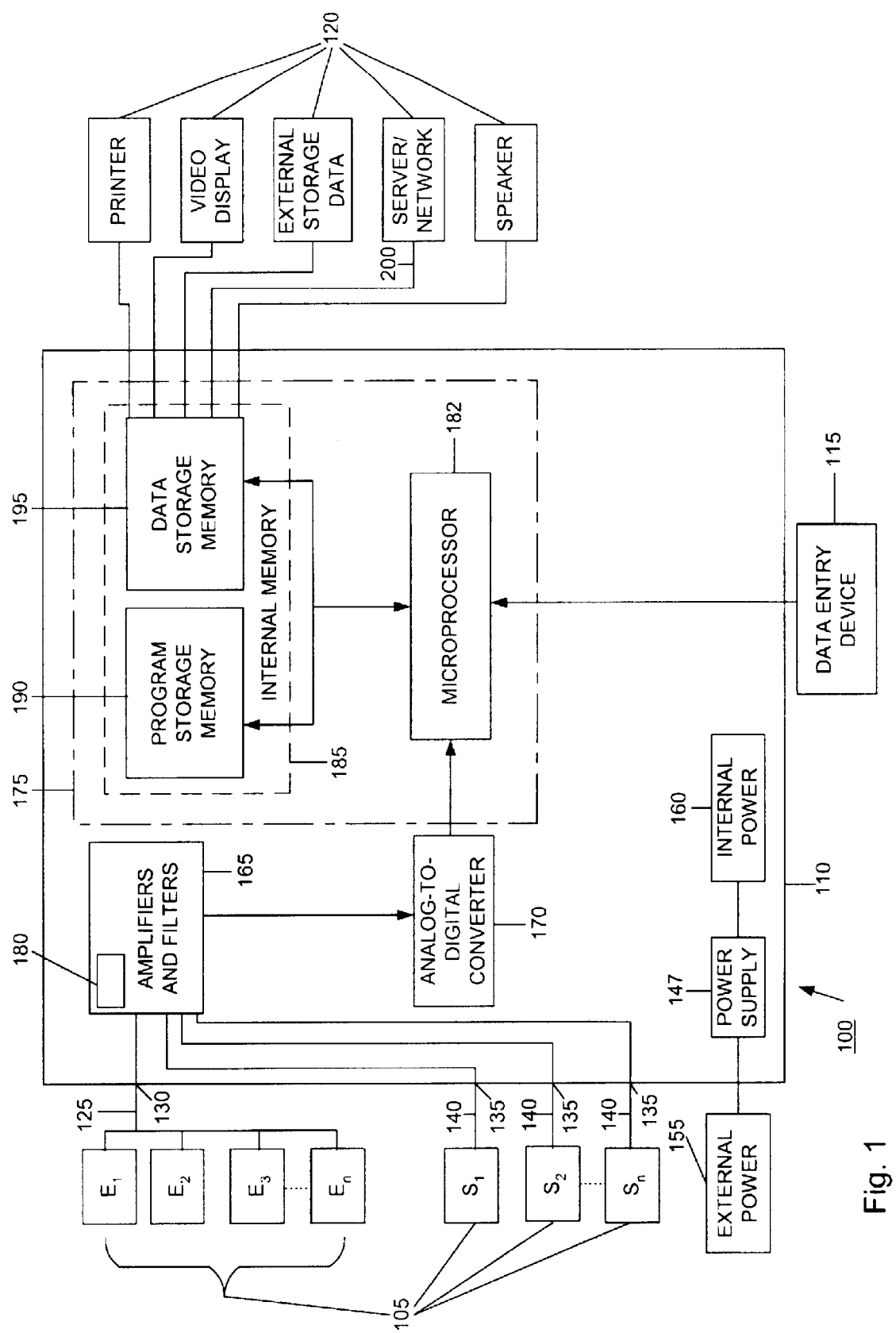
FIG. 1 is a schematic diagram of a patient monitor embodying the invention.

A patient monitor 100 embodying the invention is schematically shown in FIG. 1. An example monitor embodying the invention is a GE Medical Systems Information Technologies, Inc. DASH®3000 Pro™ brand portable monitor. In general terms, the monitor 100 includes one or more input devices 105, a central unit 110, a data entry device 115 connected to central unit 110, and one or more output devices 120 connected to central unit 110.

The one or more input devices 105 include a plurality of electrodes $E_1, E_2 \ldots E_n$ that are connectable to a patient. The electrodes acquire electrical activity (i.e., ECG signals) generated by the patient. The number of electrodes $E_1$, $E_2 \ldots E_n$ may vary. But for the embodiment shown, the number of electrodes is equal to ten and are connected to the patient in a standard twelve-lead configuration.

The electrodes $E_1, E_2, \ldots E_n$ are connected to the central unit 110 by an interface cable 125. The interface cable 125 provides direct communication between the electrodes $E_1$, $E_2 \ldots E_n$ and an input terminal 130. The interface cable 125 allows for transmission of the acquired ECG signals from the patient to the central unit 110. The interface cable 125 is preferably a passive cable but, alternatively, the cable 125 may contain active circuitry for amplifying and combining the ECG signals into ECG leads (discussed further below). In other embodiments, the electrodes $E_1, E_2 \ldots E_n$ may be in communication with the central unit 110 through a telemetry-based transmitter transmitting a radio frequency (RF) signal to one or more antennas connected to central unit 110 through a conventional RF receiver.

The one or more input devices 105 may further include one or more sensors $S_1, S_2 \ldots S_n$. The sensors $S_1, S_2 \ldots S_n$ are connectable to the patient and acquire physiological signals from the patient. Example sensors may include invasive and noninvasive blood pressure sensors, carbon dioxide sensors, pulseoximetry sensors, temperature sensors, etc. Similar to electrodes $E_1, E_2 \ldots E_n$ and for the embodiment shown, the one or more sensors $S_1, S_2 \ldots S_n$ are connected to the central processing unit at input terminals 135 by interface cables 140. In other embodiments, the one or more sensors may be in communication with the central processing unit via a telemetry transmitter as described above.

The data-entry device 115 allows an operator (e.g., a technician, nurse, doctor, etc.) to enter data into the central unit 110. The data-entry device 115 may be incorporated within the central unit 110 (e.g., a trim knob) or, alternatively, may be a stand-alone device (e.g., a stand-alone keyboard). Example data-entry devices 115 include a trim knob, a keyboard, a keypad, a touch screen, a pointing device (e.g., a mouse, a trackball), etc.

The central unit 110 includes a power supply 147. The power supply 147 powers the patient monitor 100 and receives input power either by an external power source 155 or an internal power source 160 (e.g., a battery).

The central unit 110 also includes amplifying-and-filtering circuitry 165, analog-to-digital (A/D) conversion circuitry 170, and an analysis module 175. The amplifying-and-filtering circuitry 165, the A/D conversion circuitry 170, and the analysis module 175 may be discrete circuitry, may be incorporated as an integrated circuit (e.g., an application specific integrated circuit), or may be a combination of both.

The amplifying-and-filtering circuitry 165 receives the physiological signals from the input terminals 130 and 135, and amplifies and filters (i.e., conditions) the physiological signals. For example, the amplifying-and-filtering circuitry 165 includes an instrumentation amplifier 180. The instrumentation amplifier 180 receives the ECG signals, amplifies the signals, and filters the signals to create a multi-lead ECG. The number of leads of the multi-lead ECG may vary without changing the scope of the invention.

The A/D conversion circuitry 170 is electrically connected to the instrumentation amplifier 180. The A/D conversion circuitry 170 receives the amplified and filtered physiological signals and converts the signals into digital physiological signals (e.g., a digital multi-lead ECG.) The digital physiological signals are then provided to the analysis module 175 which is electrically connected to the A/D conversion circuitry 170.

The analysis module 175 reads the digital physiological signals, analyzes the signals from the A/D conversion circuitry 170, and displays the signals and the resulting analysis to an operator. The analysis module 175 includes a controller or microprocessor 182 and internal memory 185, and implements a software program to control the monitor 100. The internal memory 185 includes program storage memory 190 for storing the software program and data storage memory 195 for storing data. The implementation of the software program, including determining a probability that the patient has acute cardiac ischemia, is discussed in further below.

The output devices 120 may include a printer, a display, a storage device (e.g., a magnetic disc drive, a read/write CD-ROM, etc.), a server or other processing unit connected via a network 200, and a speaker. Of course, other output devices may be added or attached (e.g., a defibrillator), and/or one or more output devices may be incorporated within the central unit 110. Additionally, not all of the outputs 120 are required for operation of the monitor 100.

Figure 2:
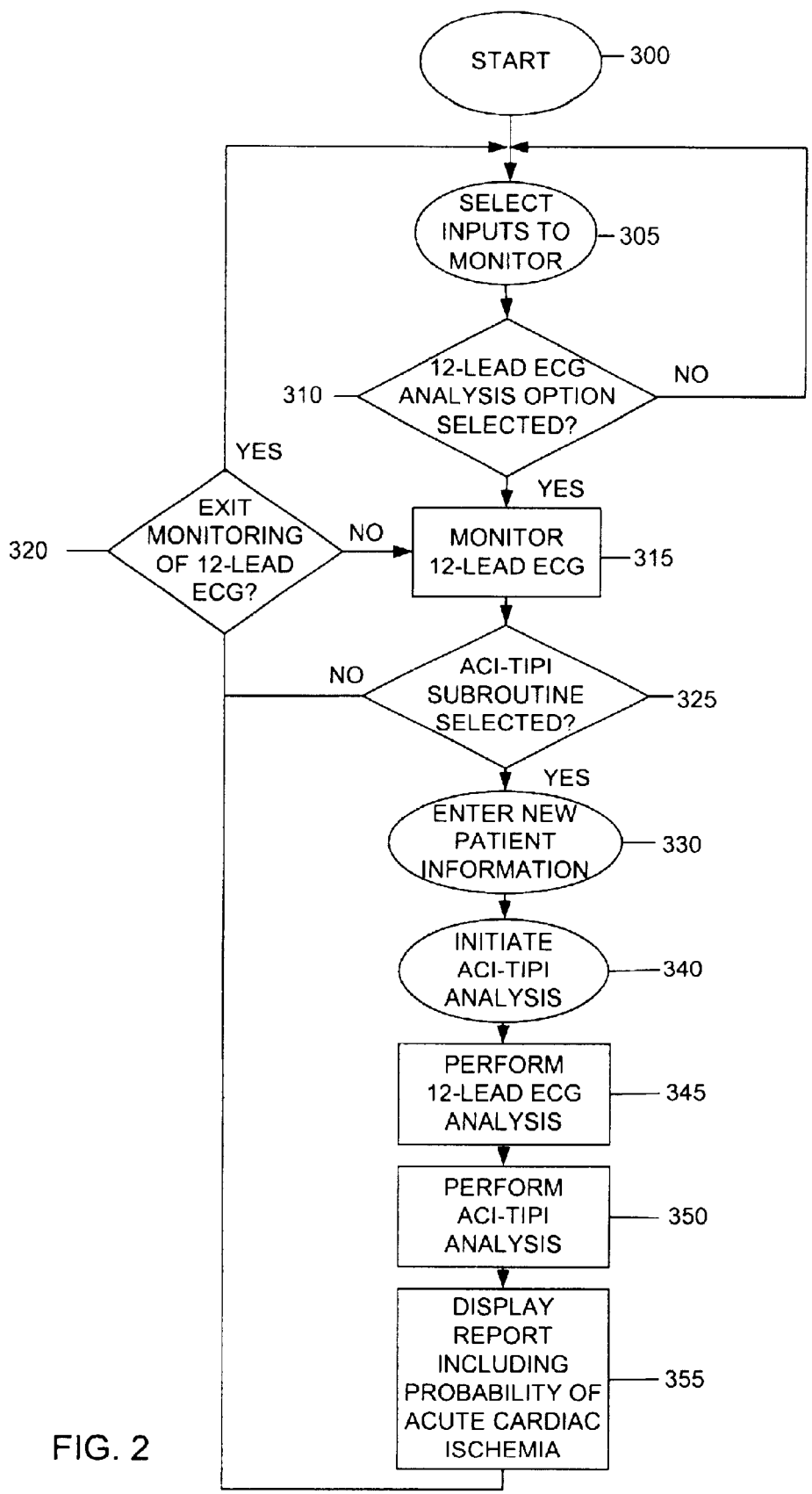
FIG. 2 is a flowchart implementing a method of determining a probability that a patient has acute cardiac ischemia.

In operation and at act 300 (FIG. 2), an operator activates the monitor 100. The software initializes the microprocessor 182. The operator then attaches the electrodes $E_1, E_2 \ldots E_n$ and/or sensors $S_1, S_2 \ldots S_n$ to the patient.

At act 305, the monitor 100 automatically identifies which input devices 105 are connected to the patient. Alternatively, the operator may inform the monitor 100, via the data-entry device 115, which inputs 105 are connected to the patient. Once the monitor 100 is informed from which inputs 105 to acquire physiological signals from, the monitor 100 begins continuously monitoring the physiological signals from the patient. The monitoring data may be displayed on the display, printed by the printer, stored in the data storage memory for analysis or later recall, provided to the external storage device for storage, and/or provided to the server via the network 200.

For example and in the embodiment shown, the operator attaches ten electrodes to the patient and selects twelve-lead ECG monitoring. Once twelve-lead ECG-monitoring is selected (act 310), the monitor 100 continuously monitors the ECG leads generated by the patient (act 315). This is accomplished by acquiring electrical activity generated by the patient in the form of ECG signals. The ECG signals are transmitted to the input terminal 130 via the interface cable 125. The ECG signals enter the central unit 110 at terminal 130 and are provided to the instrumentation amplifier 180.

The instrumentation amplifier 180 combines, amplifies and filters the ECG signals resulting in a standard twelve-lead ECG. For other electrode configurations, the number of leads of the multi-lead ECG may vary. The resulting multi-lead ECG is provided to the A/D conversion circuit 170. The A/D conversion circuit 170 samples each lead of the multi-lead ECG to create a digital signal representing the multi-lead ECG, and provides the digital multi-lead ECG to the analysis module 175. The analysis module 175 reads the digital multi-lead ECG signal for monitoring. The monitored twelve-lead ECG may be used to calculate a heart rate, detect an arrhythmia, measure ST-segment elevation and, as is discussed below, calculate a probability that the patient has acute cardiac ischemia. The monitor 100 continues to monitor the twelve-lead ECG until the operator exits the twelve-lead monitoring function (act 320). Other monitoring applications are performed similarly. The other monitoring applications include blood pressure monitoring, pulse oximetry monitoring, temperature monitoring, etc.

If the patient complains of heart pain, the operator may request the monitor 100 to perform a calculation of a probability that the patient has acute cardiac ischemia (act 325). For example, when a patient enters the emergency room complaining of heart pain, the emergency room staff may attach the patient monitor 100 to the patient for monitoring. In addition, a staff member (e.g., the resident emergency room doctor) may request a test to determine whether the patient has acute cardiac ischemia. In the past, an electrocardiograph and a technician would need to be requested and brought into the patient's direct area. The electrocardiograph would then need to be attached to the patient. Attaching the electrocardiograph to the patient takes valuable time. Moreover, the presence of another piece of equipment and the operator thereof connected to the patient, may inconvenience the emergency room staff. Thus, it is beneficial for the patient monitor 100 already connected to the patient for continuous, ongoing monitoring to be able to perform this function in addition to performing the monitoring function.

For the embodiment shown, the operator uses the data entry device 115 (e.g., the trim knob) to select an ACI-TIPI analysis. Once the ACI-TIPI analysis is selected (act 325), the software initiates an ACI-TIPI analysis subroutine (act 330). Although the patient monitor 100 described herein uses ACI-TIPI to determine a probability that the patient has acute cardiac ischemia, other instruments (i.e., formulas) may be used.

Specifically, the monitor 100 uses Formula 1 (below) to calculate or determine a probability that a patient has acute cardiac ischemia.

FORMULA 1 ACI-TIPI $$\text{probability } \% = 100 \times \left[1 - \frac{1}{1 + \exp(b_o + \sum b_i \cdot x_i)}\right]$$

where: $b_o$ is a constant term, $b_i$ are coefficients, and $x_i$ are variables. The coefficients include values representing a chest pain condition, patient demographics, and ECG analysis coefficients. The variables are empirically found and act as multipliers. Formula 1 and its constant term, coefficients and variables are further described in Selker et al., *A Tool for Judging Coronary Care Unit Admission Appropriateness, Valid for both Real-Time and Retrospective Use: Medical Care,* Vol. 28, No. 7 (July 1991), pp. 610–627 and Selker et al., *Erratum: Medical Care,* Vol. 30, No. 2 (February 1992), p. 188, both of which are incorporated herein by reference.

If the ACI-TIPI subroutine is selected, the patient monitor 100 proceeds to act 330. At act 330, the operator enters patient information. For example, the operator enters patient biographical data (e.g., patient sex and patient age) and a patient condition (e.g., chest or left arm pain is the primary complaint, chest or left arm pain is the secondary complaint, or chest or left arm pain is not present). As described above, the entered patient information is used by Formula 1 for determining a probability that a patient has acute cardiac ischemia. Other patient data may be entered when using different instruments.

Once the patient information is entered, the operator initiates the ACI-TIPI analysis (act 340) via the data entry device 115. At act 345, the software temporarily stores a portion of the monitored ECG leads for a period of time (i.e., a time window). When the ECG leads are stored, the software analyzes the stored ECG leads to obtain ECG analysis coefficients for the ACI-TIPI formula. Example ECG analysis coefficients include whether ECG Q-waves are present, whether the ECG ST segment is depressed or elevated by an amount, whether the ECG T-waves are inverted by an amount, and whether both the ECG ST segment is depressed and the ECG T-wave is inverted. The ECG analysis coefficients are used by Formula 1 to determine a probability that the patient has acute cardiac ischemia. Other ECG analysis coefficients may be used when using different instruments (i.e., different formulas). Additionally, the temporarily stored portion of the monitored ECG leads may be stored prior to the operator initiating the ACI-TIPI analysis. For example, the software may repeatedly store a portion of the monitored ECG leads for a period of time. Once the operator initiates the ACI-TIPI analysis, the software analyzes the most recently stored data to obtain ECG analysis coefficients for the ACI-TIPI formula.

At act 350, the software calculates a probability that the patient has acute cardiac ischemia using the ACI-TIPI formula as is disclosed in Selker et al., *A Tool for Judging Coronary Care Unit Admission Appropriateness, Valid for both Real-Time and Retrospective Use: Medical Care,* Vol. 28, No. 7 (July 1991), pp. 610–627 and Selker et al., *Erratum: Medical Care,* Vol. 30, No. 2 (February 1992), p. 188. Upon completing the calculation, the resulting probability is disclosed (e.g., displayed on the monitor) to the operator (act 355). In addition, the software may provide a list of factors affecting or reasons for the resulting calculated probability. Example factors are shown in TABLE 1 EXAMPLE FACTORS. Based on the probability and disclosed factors (if provided), an experienced operator may determine whether the patient should be admitted to the cardiac care unit for further testing. In addition, the resulting probability and data used for calculating the probability may be stored or printed for future reference, or provided to the network 200 for additional analysis by a remote server or processor.

TABLE 1

EXAMPLE FACTORS

| | |
|---|---|
| 1. | Chest or left arm pain present. |
| 2. | Chest or left arm pain is chief complaint. |
| 3. | Patient is male, less than 41 years of age. |
| 4. | Patient is male, age 41–50. |
| 5. | Patient is male, over 50 years of age. |
| 6. | Patient is female, less than 41 years of age. |
| 7. | Patient is female, age 41–50. |
| 8. | Patient is female, over 50 years of age. |

TABLE 1-continued

EXAMPLE FACTORS

| | |
|---|---|
| 9. | Q waves are not present. |
| 10. | No significant Q waves detected. |
| 11. | ST segment is elevated 2 mm or more. |
| 12. | ST segment is elevated 1–2 mm. |
| 13. | ST segment is depressed 2 mm or more. |
| 14. | ST segment is depressed 1–2 mm. |
| 15. | ST segment is depressed 0.5–1 mm. |
| 16. | No abnormal ST segment deviation detected. |
| 17. | Hyperactive T-waves. |
| 18. | T waves are inverted 5 mm or more. |
| 19. | T waves are inverted 1–5 mm. |
| 20. | Flattened T waves in all frontal or precordial leads. |
| 21. | No T-wave abnormality detected. |

As can be seen from the above, the invention provides a patient monitor for determining a probability that a patient has acute cardiac ischemia. The invention also provides a method of determining a probability that a patient has acute cardiac ischemia and a software tool for a patient monitor to calculate a probability that a patient has acute cardiac ischemia. Various features and advantages of the invention are set forth in the following claims.

What is claimed is:

1. A patient monitor comprising:
   a first input device connectable to a patient to acquire electrocardiogram (ECG) signals from the patient;
   an instrumentation amplifier connected to the input device to combine the signals and to generate at least one ECG lead based on the signals;
   a second input device connectable to the patient to acquire a non-ECG physiological signal; and
   an analysis module operable to continuously read the ECG lead, to analyze a portion of the ECG lead for a period of time, and to calculate a probability that the patient has acute cardiac ischemia based at least in part on the analyzed portion of the ECG lead.

2. A patient monitor as set forth in claim 1 and further comprising:
   a data entry device operable to receive patient biographical data; and
   wherein the analysis module calculates the probability that the patient has acute cardiac ischemia based at least in part on the patient biographical data.

3. A patient monitor as set forth in claim 2 wherein the patient biographical data is the sex of the patient.

4. A patient monitor as set forth in claim 2 wherein the patient biographical data is the age of the patient.

5. A patient monitor as set forth in claim 1 and further comprising a data entry device operable to receive information relating to a patient condition, and wherein the analysis module calculates a probability that the patient has acute cardiac ischemia based at least in part on the information relating to the patient condition.

6. A patient monitor as set forth in claim 5 wherein the patient condition is a reported pain located in the chest or left arm of the patient.

7. A patient monitor as set forth in claim 1 wherein the first input device is a plurality of electrodes.

8. A patient monitor as set forth in claim 1 and further comprising an output device that informs an operator of the probability that the patient has acute cardiac ischemia.

9. A patient monitor as set forth in claim 8 wherein the output device is a display.

10. A patient monitor as set forth in claim 8 wherein the output device is a printer.

11. A patient monitor as set forth in claim 1 wherein the analysis module includes a memory unit, a processor, and software stored in the memory unit that operates the processor.

12. A patient monitor as set forth in claim 11 wherein the software operates the processor to analyze a portion of the ECG lead for a period of time resulting in at least one ECG analysis coefficient, and to calculate a probability that the patient has acute cardiac ischemia based at least in part on the ECG analysis coefficient.

13. A patient monitor as set forth in claim 12 wherein the ECG analysis coefficient signifies whether an ECG Q-wave is present.

14. A patient monitor as set forth in claim 12 wherein the ECG analysis coefficient signifies whether an ECG ST segment is depressed or elevated.

15. A patient monitor as set forth in claim 12 wherein the ECG analysis coefficient signifies whether an ECG T-wave is inverted.

16. A patient monitor comprising:
    an input device connectable to a patient to acquire electrocardiogram (ECG) signals from the patient;
    an instrumentation amplifier connected to the input device to combine the signals and to generate at least one ECG lead based on the signals;
    an analysis module operable to continuously read the ECG lead, to analyze a portion of the ECG lead for a period of time, and to calculate a probability that the patient has acute cardiac ischemia based at least in part on the analyzed portion of the ECG lead;
    an output device that informs an operator of the probability that the patient has acute cardiac ischemia;
    an output terminal connectable to a second processor via a network; and
    wherein the output device is the second processor.

17. A patient monitor comprising:
    an input device connectable to a patient to acquire electrocardiogram (ECG) signals from the patient;
    an instrumentation amplifier connected to the input device to combine the signals and to generate at least one ECG lead based on the signals;
    an analysis module operable to continuously read the ECG lead, to analyze a portion of the ECG lead for a period of time, and to calculate a probability that the patient has acute cardiac ischemia based at least in part on the analyzed portion of the ECG lead; and
    wherein the patient monitor is powered by a direct current power source.

18. A patient monitor comprising:
    an input device connectable to a patient to acquire electrocardiogram (ECG) signals from the patient;
    an instrumentation amplifier connected to the input device to combine the signals and to generate at least one ECG lead based on the signals;
    an analysis module operable to continuously read the ECG lead, to analyze a portion of the ECG lead for a period of time, and to calculate a probability that the patient has acute cardiac ischemia based at least in part on the analyzed portion of the ECG lead; and
    wherein the patient monitor is powered by an alternating current power source.

19. A patient monitor comprising:
    an input device connectable to a patient to acquire electrocardiogram (ECG) signals from the patient;

an instrumentation amplifier connected to the input device to combine the signals and to generate at least one ECG lead;

a second input device connectable to the patient to acquire a non-ECG physiological signal;

a data entry device operable to receive patient biographical data and information relating to a patient condition; and an analysis module including a memory unit, a processor, and software that operates the processor to continuously read the ECG lead, to continuously read the non-ECG physiological signal, to analyze a portion of the ECG for a period of time, and to calculate a probability that the patient has acute cardiac ischemia based at least in part on the analyzed portion of the ECG lead, the patient biographical data and the information relating to the patient condition.

20. A patient monitor as set forth in claim 19 wherein the patient biographical data is the sex of the patient.

21. A patient monitor as set forth in claim 19 wherein the patient biographical data is the age of the patient.

22. A patient monitor as set forth in claim 19 wherein the patient condition is a reported pain located in the chest or left arm of the patient.

23. A patient monitor as set forth in claim 19 wherein the software operates the processor to analyze a portion of the ECG lead for a period of time resulting in at least one ECG analysis coefficient, and to calculate a probability that the patient has acute cardiac ischemia based at least in part on the ECG analysis coefficient.

24. A patient monitor as set forth in claim 23 wherein the ECG analysis coefficient signifies whether an ECG Q-wave is present.

25. A patient monitor as set forth in claim 23 wherein the ECG analysis coefficient signifies whether an ECG ST segment is depressed or elevated.

26. A patient monitor as set forth in claim 23 wherein the ECG analysis coefficient signifies whether an ECG T-wave is inverted.

27. A patient monitor as set forth in claim 19 and further comprising an output device that informs an operator of the probability that the patient has acute cardiac ischemia.

28. A patient monitor as set forth in claim 19 wherein the patient monitor is powered by a direct current power source.

29. A patient monitor as set forth in claim 19 wherein the patient monitor is powered by a alternating current power source.

30. A method of determining a probability that a patient has acute cardiac ischemia, the method comprising the acts of:

providing a patient monitor having an input device connectable to a patient;

acquiring electrocardiogram (ECG) signals from the patient;

generating at least one ECG lead in response to acquiring the ECG signals;

continuously monitoring the ECG lead;

analyzing a portion of the ECG lead for a period of time;

calculating the probability that the patient has acute cardiac ischemia based at least in part on the analyzed portion of the ECG lead; and wherein the act of continuously monitoring the ECG lead includes continuously displaying the ECG lead.

31. A method of determining a probability that a patient has acute cardiac ischemia, the method comprising the acts of:

providing a patient monitor having an input device connectable to a patient;

acquiring electrocardiogram (ECG) signals from the patient;

generating at least one ECG lead in response to acquiring the ECG signals;

continuously monitoring the ECG lead;

analyzing a portion of the ECG lead for a period of time;

calculating the probability that the patient has acute cardiac ischemia based at least in part on the analyzed portion of the ECG lead; and wherein the act of continuously monitoring the ECG lead includes continuously recording the ECG lead.

32. A method of determining a probability that a patient has acute cardiac ischemia, the method comprising the acts of:

providing a patient monitor having a first input device connectable to a patient;

acquiring electrocardiogram (ECG) signals from the patient;

generating at least one ECG lead in response to acquiring the ECG signals;

continuously monitoring the ECG lead;

analyzing a portion of the ECG lead for a period of time;

calculating the probability that the patient has acute cardiac ischemia based at least in part on the analyzed portion of the ECG lead;

wherein the patient monitor includes a second input device that connects to the patient and acquires a non-ECG physiological signal; and wherein the method further comprises continuously monitoring the non-ECG physiological signal from the patient.

33. A method as set forth in claim 32 wherein the patient monitor includes a data entry device that receives patient biographical data, wherein the method further comprises the act of entering patient biographical data via the data entry device, and wherein the act of calculating includes calculating the probability of acute cardiac ischemia based at least in part on the patient biographical data.

34. A method as set forth in claim 33 wherein the patient biographical data is the sex of the patient.

35. A method as set forth in claim 34 wherein the patient biographical data is the age of the patient.

36. A method as set forth in claim 32 wherein the patient monitor includes a data entry device that receives a patient condition, wherein the method further comprises the act of entering the patient condition via the data entry device, and wherein the act of calculating includes calculating the probability of acute cardiac ischemia based at least in part on the patient condition.

37. A method as set forth in claim 36 wherein the patient condition is a reported pain located in the chest or left arm of the patient.

38. A method as set forth in claim 32 wherein the input device is a plurality of electrodes.

39. A method as set forth in claim 32 wherein the act of analyzing the ECG lead comprises analyzing a portion of the ECG lead for a period of time resulting in at least one ECG analysis coefficient, and wherein the act of calculating comprises calculating the probability of the patient having acute cardiac ischemia based at least in part on the ECG analysis coefficient.

40. A method as set forth in claim 39 wherein the ECG analysis coefficient signifies whether an ECG Q-wave is present.

41. A method as set forth in claim 39 wherein the ECG analysis coefficient signifies whether an ECG ST segment is depressed or elevated.

42. A method as set forth in claim 39 wherein the ECG analysis coefficient signifies whether an ECG T-wave is inverted.

43. A method as set forth in claim 32 and further comprising informing an operator of the probability of the patient having acute cardiac ischemia.

44. A software program stored in a computer readable medium for operation in a patient monitor to determine a probability that a patient has acute cardiac ischemia, the software program comprising program code for:

reading at least one electrocardiogram (ECG) lead acquired from the patient;

continuously monitoring the ECG lead;

analyzing a portion of the ECG lead for a period of time;

calculating the probability that the patient has acute cardiac ischemia based at least in part on the analyzed portion of the ECG lead; and wherein the continuously monitoring act includes continuously display the ECG lead.

45. A software program stored in a computer readable medium for operation in a patient monitor to determine a probability that a patient has acute cardiac ischemia, the software program comprising program code for:

reading at least one electrocardiogram (ECG) lead acquired from the patient;

continuously monitoring the ECG lead;

analyzing a portion of the ECG lead for a period of time;

calculating the probability that the patient has acute cardiac ischemia based at least in part on the analyzed portion of the ECG lead; and wherein the continuously monitoring act includes continuously recording the ECG lead.

46. A software program stored in a computer readable medium for operation in a patient monitor to determine a probability that a patient has acute cardiac ischemia, the software program comprising program code for:

reading at least one electrocardiogram (ECG) lead acquired from the patient;

continuously monitoring the ECG lead;

analyzing a portion of the ECG lead for a period of time;

calculating the probability that the patient has acute cardiac ischemia based at least in part on the analyzed portion of the ECG lead;

receiving patient biographical data; and wherein the act of calculating includes calculating the probability of acute cardiac ischemia based at least in part on the patient biographical data.

47. A software program as set forth in claim 46 wherein the patient biographical data is the sex of the patient.

48. A software program as set forth in claim 47 wherein the patient biographical data is the age of the patient.

49. A software program stored in a computer readable medium for operation in a patient monitor to determine a probability that a patient has acute cardiac ischemia, the software program comprising program code for:

reading at least one electrocardiogram (ECG) lead acquired from the patient;

continuously monitoring the ECG lead;

analyzing a portion of the ECG lead for a period of time;

calculating the probability that the patient has acute cardiac ischemia based at least in part on the analyzed portion of the ECG lead;

receiving a patient condition; and wherein the act of calculating includes calculating the probability of acute cardiac ischemia based at least in part on the patient condition.

50. A software program as set forth in claim 49 wherein the patient condition is a reported pain located in the chest or left arm of the patient.

51. A software program stored in a computer readable medium for operation in a patient monitor to determine a probability that a patient has acute cardiac ischemia, the software program comprising program code for:

reading at least one electrocardiogram (ECG) lead acquired from the patient;

continuously monitoring the ECG lead;

analyzing a portion of the ECG lead for a period of time;

calculating the probability that the patient has acute cardiac ischemia based at least in part on the analyzed portion of the ECG lead;

reading at least one non-ECG physiological signal; and continuously monitoring the non-ECG physiological signal.

52. A software program as set forth in claim 51 wherein the act of analyzing the ECG lead comprises analyzing a portion of the ECG lead for a period of time resulting in at least one ECG analysis coefficient, and wherein the act of calculating comprises calculating the probability of the patient having acute cardiac ischemia based at least in part on the ECG analysis coefficient.

53. A software program as set forth in claim 52 wherein the ECG analysis coefficient signifies whether an ECG Q-wave is present.

54. A software program as set forth in claim 52 wherein the ECG analysis coefficient signifies whether an ECG ST segment is depressed or elevated.

55. A software program as set forth in claim 52 wherein the ECG analysis coefficient signifies whether an ECG T-wave is inverted.

* * * * *